United States Patent
Sklar et al.

(10) Patent No.: US 6,890,487 B1
(45) Date of Patent: May 10, 2005

(54) FLOW CYTOMETRY FOR HIGH THROUGHPUT SCREENING

(75) Inventors: Larry A. Sklar, Albuquerque, NM (US); Bruce S. Edwards, Albuquerque, NM (US); Frederick W. Kuckuck, Albuquerque, NM (US)

(73) Assignee: Science & Technology Corporation ©UNM, Albuquerque, NM (US)

( * ) Notice: Subject to any disclaimer, the term of this patent is extended or adjusted under 35 U.S.C. 154(b) by 0 days.

(21) Appl. No.: 09/501,643

(22) Filed: Feb. 10, 2000

Related U.S. Application Data

(60) Provisional application No. 60/156,946, filed on Nov. 9, 1999.

(51) Int. Cl.[7] .................. G01N 7/00; G01N 33/00
(52) U.S. Cl. .................. 422/93; 422/50; 422/55; 422/63; 422/68.1; 422/81; 422/82; 422/82.08; 422/100; 435/286.5; 435/286.6; 435/287.1; 435/287.3; 435/287.6; 435/288.4; 435/288.5; 436/52; 436/53; 436/54; 436/165; 436/172; 436/180
(58) Field of Search ................ 422/50, 55, 63, 422/65, 68.1, 81, 82, 82.08, 93, 100; 436/286.5, 286.6, 287.1, 287.3, 287.6, 288.4, 288.5, 52, 53, 54, 165, 172, 180; 435/286.5, 286.6, 287.1, 287.3, 287.6, 288.4

(56) References Cited

U.S. PATENT DOCUMENTS

| | | |
|---|---|---|
| 3,698,870 A | 10/1972 | DeJong |
| 3,921,439 A | 11/1975 | Burns |
| 4,053,282 A | 10/1977 | Hach et al. |
| 4,116,631 A | 9/1978 | Trinel et al. |
| 4,177,677 A | 12/1979 | Ruzicka et al. |
| 4,224,033 A | 9/1980 | Hansen et al. |
| 4,399,225 A | 8/1983 | Hansen et al. |
| 4,661,913 A | 4/1987 | Wu et al. |
| 4,853,336 A | 8/1989 | Saros et al. |
| 4,957,009 A | 9/1990 | Nohl et al. |
| 5,080,866 A | 1/1992 | Petty et al. |
| 5,221,521 A | 6/1993 | Hashizume et al. |
| 5,268,147 A | 12/1993 | Zabetakis et al. |
| 5,286,452 A | 2/1994 | Hansen |
| 5,369,037 A | 11/1994 | Hansen |
| 5,374,398 A | 12/1994 | Isami et al. |
| 5,395,588 A | 3/1995 | North et al. |
| 5,464,752 A | 11/1995 | Kortright et al. |
| 5,488,469 A | 1/1996 | Yamamoto et al. |
| 5,504,010 A | 4/1996 | Mitani et al. |
| 5,532,154 A | 7/1996 | Brown |
| 5,641,457 A | 6/1997 | Vardanega et al. |
| 5,694,486 A | 12/1997 | Shigeeda et al. |
| 5,739,036 A | 4/1998 | Parris |
| 5,776,781 A | 7/1998 | Vardanega et al. |
| 5,788,927 A | 8/1998 | Farrell et al. |
| 5,824,269 A | 10/1998 | Kosaka et al. |
| 5,834,314 A | 11/1998 | Gates et al. |
| 6,132,685 A | * 10/2000 | Kercso et al. ............ 422/104 |
| 6,150,180 A | * 11/2000 | Parce et al. ............ 436/514 |
| 6,156,178 A | * 12/2000 | Mansfield et al. .......... 204/457 |
| 6,159,739 A | * 12/2000 | Weigl et al. ............ 436/52 |

OTHER PUBLICATIONS

Lindberg et al., "Flow Injection Cytometry: A New Approach for Sample and Solution Handling in Flow Cytometry," *Cytometry* 14:230–236 (1993).

Pennings et al., "Improved Flow Cytometry of Cellular DNA and RNA by On–Line Reagent Addition," *Cytometry* 8:335–338 (1987).

Zhao et al., "A Flow Injection Flow Cytometry System for Online Monitoring of Bioreactors," *Biotechnology and Bioengineering* v62:609–617, Analyst. Biotechtol Bioeng Mar. 1999 Abstract Only.

Deandrade et al., "High Performance Modular Spectrophotometric Flow Cell," *Analyst*, v. 116:905–907, 1991. Abstract Only.

Zhi ZL, "Segmental Flow–Injection Analysis, A Hybrid Technique of Segmented Continuous–Flow Analysis, a Hybrid Technique of Segmented Continuous–Flow Analysis and Flow–Injection Analysis," *Analysis* Trac–Trends in Mal. Chem. 17(7):411–417 (Aug. 1998) Abstract Only.

Hodder, P.S., et al., "Microfabricated Flow Chamber for Fluorescence–Based Chemistries and Stopped–Flow Injection Cytometry," Analyst, vol. 122, pp. 883–887, (Sep. 1997).

Nolan, J. P., et al., "A Rapid Mix Flow Cytometer with Subsecond Kinetic Resolution," Cytometry, vol. 21, pp 223–229 (1995).

Nolan, J. P., et al., "The Emergence of Flow Cytometry for Sensitive, Real–Time Measurements of Molecular Interactions," Nature Biotechnology, vol. 16, pp 633–638 (Jul. 1998).

* cited by examiner

*Primary Examiner*—Long V. Le
*Assistant Examiner*—Gailene R. Gabel
(74) *Attorney, Agent, or Firm*—R. Neil Sudol; Henry D. Coleman; William J. Sapone

(57) ABSTRACT

The present invention, provides a flow cytometry apparatus for the detection of particles from a plurality of samples comprising: means for moving a plurality of samples comprising particles from a plurality of respective source wells into a fluid flow stream; means for introducing a separation gas between each of the plurality of samples in the fluid flow stream; and means for selectively analyzing each of the plurality of samples for the particles. The present invention also provides a flow cytometry method employing such an apparatus.

34 Claims, 5 Drawing Sheets

FLOW CYTOMETRY FOR HIGH THROUGHPUT SCREENING

CROSS-REFERENCE TO RELATED APPLICATIONS

This application makes reference to co-pending U.S. Provisional Patent Application No. 60/156,946, entitled "Flow Cytometry Real-Time Analysis of Molecular Interactions," filed Nov. 9, 1999. The entire contents and disclosure of this application is hereby incorporated by reference.

GOVERNMENT INTEREST STATEMENT

This invention is made with government support under contract number NIH 1R24 GM 60799 (Project Number 3). The government may have certain rights in this invention.

BACKGROUND OF THE INVENTION

1. Field of the Invention

The present invention relates to a flow cytometry apparatus.

2. Description of the Prior Art

Flow cytometry is used to characterize cells and particles by making measurements on each at rates up to thousands of events per second. The measurement consists of simultaneous detection of the light scatter and fluorescence associated with each event. Commonly, the fluorescence characterizes the expression of cell surface molecules or intracellular markers sensitive to cellular responses to drug molecules. The technique often permits homogeneous analysis such that cell associated fluorescence can often be measured in a background of free fluorescent indicator. The technique often permits individual particles to be sorted from one another.

However, a deficiency with conventional flow cytometry is that it does not allow for the analysis of multiple samples consisting of multiple cells or particles in a rapid manner, a fact that has limited the uses of flow cytometry in drug discovery. For example, the industrial standard for high throughput drug discovery is 100,000 samples per day. Because of its low throughput, flow cytometry has generally not been considered applicable to high throughput screening in drug discovery.

SUMMARY OF THE INVENTION

It is therefore an object of the present invention to provide a flow cytometry apparatus that meets the needs of high throughput screening.

According to one aspect of the present invention, there is provided a flow cytometry apparatus for the detection of particles from a plurality of samples comprising: means for moving a plurality of samples comprising particles from a plurality of respective source wells into a fluid flow stream; means for introducing a separation gas between each of the plurality of samples in the fluid flow stream; and means for selectively analyzing each of the plurality of samples for the particles.

According to a second aspect of the present invention, there is provided a method for analyzing a plurality of samples comprising: moving a plurality of samples comprising particles into a fluid flow stream; separating adjacent ones of the plurality of samples from each other in the fluid flow stream by a separation gas; and selectively analyzing each of the plurality of samples for the particles.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Figure 1A:
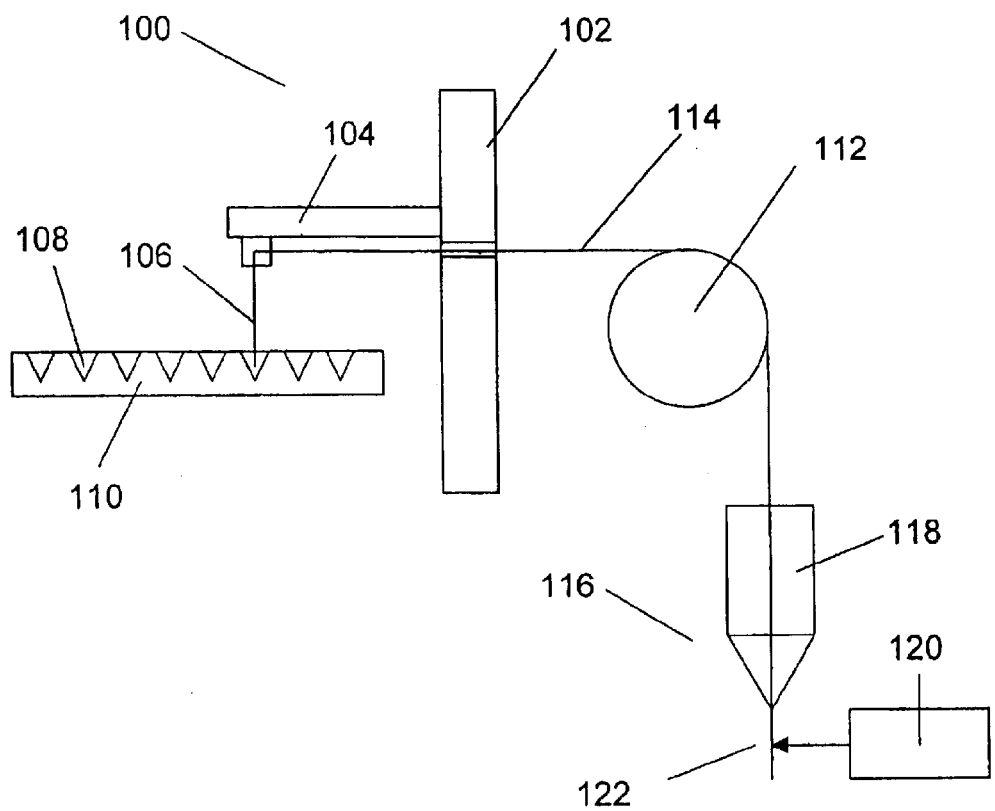
FIG. 1A is a schematic view of a flow cytometry apparatus constructed in accordance with a preferred embodiment of the invention.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "particles" refers to any particles that may be detected using a flow cytometry apparatus.

For the purposes of the present invention, the term "biomaterial" refers to any organic material obtained from an organism, either living or dead. The term "biomaterial" also refers to any synthesized biological material such as synthesized oligonucleotides, synthesized polypeptides, etc. The synthesized biological material may be a synthetic version of a naturally occurring biological material or a non-naturally occurring biological made from portions of naturally occurring biological materials, such as a fusion protein, or two biological materials that have been bound together, such as an oligonucleotide, such as DNA or RNA, bound to a peptide, either covalently or non-covalently, that the oligonucleotide does not normally bind to in nature.

For the purposes of the present invention, the term "oligonucleotide" refers to any oligonucleotide, including double and single-stranded DNA, RNA, PNAs (peptide nucleic acids) and any sequence of nucleic acids, either natural or synthetic, derivatized or underivatized.

For the purposes of the present invention the term "peptide" refers to all types of peptides and conjugated peptides including: peptides, proteins, polypeptides, protein sequences, amino acid sequences, denatured proteins, antigens, oncogenes and portions of oncogenes.

For the purposes of the present invention, the term "organism" refers not only to animals, plants, bacteria, viruses, etc. but also to cell cultures, reproduced oligonuncleotides, etc. made from organic material obtained from animals, plants, bacteria, viruses, etc.

For the purposes of the present invention, the term "source well" refers to any well on a well plate, whether or not the source well contains a sample. For the purposes of the present invention, the term "sample source well" refers to a source well containing a sample.

For the purposes of the present invention, the term "sample" refers to a fluid solution or suspension containing particles to be analyzed using a method and/or apparatus of the present invention. The particles to be analyzed in a sample may be tagged, such as with a fluorescent tag. The particles to be analyzed may also be bound to a bead, a receptor, or other useful protein or polypeptide, or may just be present as free particles, such as particles found naturally in a cell lysate, purified particles from a cell lysate, particles from a tissue culture, etc. The sample may include chemicals, either organic or inorganic, used to produce a reaction with the particles to be analyzed. When the particles to be analyzed are biomaterials, drugs may be added to the samples to cause a reaction or response in the biomaterial particles. The chemicals, drugs or other additives may be added to and mixed with the samples when the samples are in sample source wells or the chemicals, drugs or other additives may be added to the samples in the fluid flow stream after the samples have been intaken by the autosampler.

For the purposes of the present invention, the term "adjacent samples" refers to two samples in a fluid flow stream that are separated from each other by a separation gas, such as an air bubble. For the purposes of the present invention, the term "immediately adjacent samples" refers to adjacent samples that are only separated from each other by a separation gas. For the purposes of the present invention, "buffer fluid separated adjacent samples" refers to adjacent samples that are separated from each other by two separation gas bubbles and a buffer fluid, with the buffer fluid being located between the two separation gas bubbles.

For the purposes of the present invention, the term "separation gas" refers to any gas such as air, an inert gas, or fluid etc. that can be used to form a gas bubble or immiscible fluid between adjacent samples or between a sample and a buffer fluid. An immiscible fluid is a fluid that will not substantially mix with and contaminate a sample.

For the purposes of the present invention, the term "buffer fluid" refers to a fluid that is substantially free of the particles to be detected by the apparatus and method of the present invention.

For the purposes of the present invention, the term "drug" refers to any type of substance that is commonly considered a drug. For the purposes of the present invention, a drug may be a substance that acts on the central nervous system of an individual, e.g. a narcotic, hallucinogen, barbiturate, or a psychotropic drug. For the purposes of the present invention, a drug may also be a substance that kills or inactivates disease-causing infectious organisms. In addition, for the purposes of the present invention, a drug may be a substance that affects the activity of a specific cell, bodily organ or function. A drug may be an organic or inorganic chemical, a biomaterial, etc.

For the purposes of the present invention, the term "plurality" refers to two or more of anything, such as a plurality of samples.

For the purposes of the present invention, the term "homogenous" refers to a plurality of identical samples. The term "homogenous" also refers to a plurality of samples that are indistinguishable with respect to a particular property being measured by an apparatus or a method of the present invention.

For the purposes of the present invention, the term "heterogeneous" refers to a plurality of samples in a fluid flow stream in which there are at least two different types of samples in the fluid flow stream. One way a heterogeneous plurality of samples in a fluid flow stream of the present invention may be obtained is by intaking different samples from different source wells in a well plate. Another way of obtaining a heterogeneous plurality of samples is by intaking different samples from identical source wells at various time points where a reaction or a series of reactions is or had been occurring.

For the purposes of the present invention, the term "fluid flow stream" refers to a stream of fluid samples, separated by one or more bubbles of a separation gas and/or one or more portions of a buffer fluid.

For the purposes of the present invention, the term "fluid flow path" refers to device such as a tube, channel, etc. through which a fluid flow stream flows. A fluid flow path may be composed of several separate devices, such as a number of connected or joined pieces of tubing or a single piece of tubing, alone or in combination with channels or other different devices.

For the purposes of the present invention, the term "high speed multi-sample tube" refers to any tube that may be used with a peristaltic pump that has compression characteristics that allow a peristaltic pump to move samples separated by a separation gas through the tube at a speed of at least 6 samples per minute without causing adjacent samples to mix with each other. An example of such a tube is a polyvinylchloride (PVC) tube having an inner diameter of about 0.01 to 0.03 inches and a wall thickness of about 0.01 to 0.03 inches. A particularly preferred tube is a PVC tube having an inner diameter of about 0.02 inches and a wall thickness of about 0.02 inches.

Description

There have been several efforts at automated sample handling in flow cytometry. For, example, both Coulter Instrument Co. and Becton-Dickinson have sold sample handling systems that use carousels to handle samples from standard sized tubes. These systems typically intake samples at a rate of ~1 tube of sample per minute.

There has also been some effort to intake samples from 96 well plates. For example at the ISAC meeting in 1998 at Colorado Springs, Coulter Instrument Co. showed a TECAN sampling system for 96 well plates that sampled at about the rate of 3 samples per 2 minutes. Becton-Dickinson is presently developing a system with similar characteristics. Luminex Corp. (Austin, Tex.) is developing a system that samples at rates of 2–4 samples/minute. It puts a multi-well plate on a movable stage that brings it into position with a syringe controlled sample line.

Other groups have also used valves and syringes in flow cytometry, most notably, the "flow injection" group, Lindberg et al. at University of Washington. One group, Zhao et al. at the University of Minnesota, has recently reported the use of air bubbles in flow cytometry to separate samples. However, in none of the processes described above is there any mention of throughput speed (samples/minute). A group at the University of New Mexico has used plug flow cytometry and achieved sampling rates of at least 6 samples per minute, see U.S. patent application Ser. No. 09/330,259, the entire disclosure and contents of which is hereby incorporated by reference. Furthermore, in the published descriptions of these processes, the problems with bubbles disrupting flow cytometry were also pointed out.

The present invention uses a separation gas, such as air bubbles, to separate samples introduced from an autosampler into a tubing line that directly connects the autosampler and a flow cytometer. A peristaltic pump between the two devices moves the fluid. The air bubbles appear to be most effective at separating samples when there are no junctions or valves in the line. These junctions disturb or break up the bubbles and appear to allow the separated samples to come into contact with one another. Peristaltic flow rates of ~3 ul/second through common tubing (0.02 inch tubing, 10 rpm or higher) have already been determined to be compatible with flow cytometric detection.

Figure 1B:
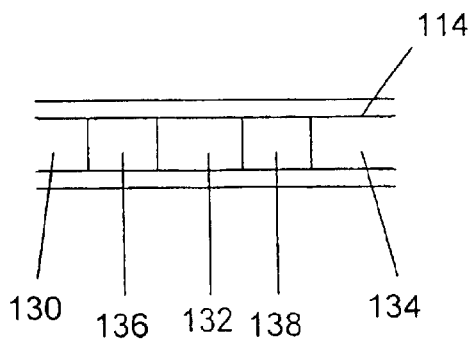
FIG. 1B is a cross-sectional schematic view of immediately adjacent samples in a tube of the flow cytometry apparatus of FIG. 1A.

FIG. 1A illustrates a preferred flow cytometry apparatus 100 of the present invention. Flow cytometry apparatus 100 includes a conventional autosampler 102 having an adjustable arm 104 on which is mounted a hollow probe 106. As arm 104 moves back and forth (left and right in FIG. 1) and side to side (into and out of the plane of FIG. 1), probe 106 is lowered into individual source wells 108 of a well plate 110 to obtain a sample that has been tagged with a fluorescent tag (not shown in FIG. 1) to be analyzed using flow cytometry apparatus 100. Once a sample is picked up by probe 106, a peristaltic pump 112 forces the sample through a tube 114 that extends from autosampler 102 through peristaltic pump 112 and into a flow cytometer 116 including a flow cell 118 and a laser interrogation device 120. Laser interrogation device 120 examines individual samples flowing from flow cell 118 at a laser interrogation point 122. In between intaking sample material from each of source wells 108, probe 106 is allowed to intake air, thereby forming an air bubble between each adjacent sample. FIG. 1B illustrates series of samples 130, 132 and 134 separated from each other by air bubbles 136 and 138 in tube 114. In FIG. 1B, sample 130 is immediately adjacent to sample 132, and sample 132 is immediately adjacent to sample 134.

When samples 130, 132 and 134 pass through laser interrogation point 122, the particles in the samples are sensed by flow cytometer 116 due to the fluorescent tag on the particles. In contrast, when air bubbles 136 and 138 pass through laser interrogation point 122, no particles are sensed. Therefore, a graph of the data points of fluorescence sensed versus time for a series of samples analyzed using the flow cytometer of the present invention will form distinct groups, each aligned with the time that a sample containing particles passes through the laser interrogation point. In order to detect the presence of each of two or more different types of samples, in a heterogeneous plurality of samples, each of the two or more different types of samples may be tagged with different fluorescent tags, different amounts of a single tag or some combination of different tags and different amount of a single tag. In such a case, the groupings of data points will vary vertically on a fluorescence versus time graph, depending on which type of sample is being sensed. As with the case of sensing a single type of sample, each sensed sample will exhibit a group of data points aligned with the time that the sample passes through the laser interrogation point.

Figure 1C:
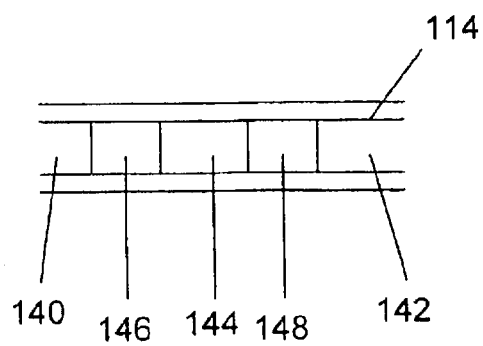
FIG. 1C is a cross-sectional schematic view of buffer fluid separated adjacent samples in a tube of the flow cytometry apparatus of FIG. 1A.

In an alternative embodiment of the present invention using the flow cytometry apparatus of FIG. 1A, some of the source wells on the well plate of the apparatus illustrated in FIG. 1A may contain a buffer solution to allow for the formation of buffer fluid separated adjacent samples in a tube through which samples pass. When this is the case, after each sample is picked up by the probe, the probe intakes air, then is lowered into a source well containing buffer solution, then the probe intakes air again, and then the probe intakes a second sample. This sequence may then be repeated for samples which the probe subsequently intakes. FIG. 1C shows how two buffer fluid separated adjacent samples 140 and 142 are separated from each other by buffer fluid 144 and two air bubbles 146 and 148 in tube 114. When samples 140 and 142 pass through laser interrogation point 122, the particles in the samples are sensed by the flow cytometer due to the fluorescent tag on the particles. In contrast, when buffer fluid 144, and air bubbles 146 and 148 pass through laser interrogation point 122, no particles are sensed. Therefore, a graph of the data points of fluorescence sensed versus time for a series of samples analyzed using the flow cytometer of the present invention will form distinct groups, each aligned with the time that a sample containing particles passes through the laser interrogation point. In order to detect the presence of two or more different types of samples, each of the two or more different types of samples may be tagged with different fluorescence tags or different amounts of a single tag. In such a case, the groupings of data points will vary vertically on a fluorescence versus time graph, depending on which type of sample is being sensed. As with the case of sensing a single type of sample, each sensed sample will exhibit a group of data points aligned with the time that the sample passes through the laser interrogation point.

Alternatively, buffer fluid separated adjacent samples may be formed by providing a reservoir of buffer fluid in or attached to the autosampler to inject buffer fluid into the tube for the fluid flow stream. In this case, after each sample is picked up by the probe, the probe intakes air, then buffer fluid is injected into the tube for the fluid flow stream, then the probe intakes air again, and then the probe intakes a second sample. This sequence may then be repeated for subsequent samples to be separated by a buffer fluid.

The present invention is compatible with relatively inexpensive commercial well plates for use with autosamplers from 96 well plates to 384 well plates to at least as many as 1536 well plates. The source wells of the present invention may be all filled with samples and/or buffer fluids, or some may be left empty. When there are a plurality of different types of samples in the source wells of a well plate, the sample types may be arranged in the order in which they are taken up by the probe, or the sample types may be arranged in any other convenient arrangement. For example, all of the source wells in a one row of source wells may contain one sample type and all of the source wells of a second row may contain a second sample type.

The source wells may be made any conventional shape used for source wells in a well plate for an autosampler. Preferably, when small amounts of sample are used in each source well, the source wells are conical in shape, as illustrated in FIG. 1A, to allow even the smallest amounts of sample to be withdrawn by the probe or to allow the particles to concentrate in the bottom of the well. The use of a well plate with conical source wells reduces the problems associated with the settling of particles to the bottom of the well prior to being intaken by the probe. An alternative means to circumvent particle settling would be to sample from wells in an inverted plate given an appropriate well dimensions that will permit sample retention in the well (e.g. by capillary forces) when the plate is in this position.

The autosampler of the present invention may be any conventional autosampler suitable for intaking samples from a well plate. A preferred type of autosampler is the Gilson 215 liquid manager.

The use of automation in plate delivery and retrieval for the autosampler may allow automation of the overall screening process.

One preferred probe for the present invention is a 0.01 inch ID, 1/15 inch OD stainless steel needle compatible with HPLC ferrule fittings. A Gilson interface module for bidirectional communication between an MS DOS computer and a probe manipulating arm and peristaltic pump. Software designed using commercial languages, such as Microsoft Visual C++, may be used to control the speed and distance of probe motions in all 3 dimensions, the sensing of probe contact with liquid in a source well to assure reproducible sample volumes, and the speed of the peristaltic pump. A computer or other known device may be used to control the autosampler to regulate sample size and bubble size by varying the time that the probe is in a source well or above a source well. Also, various sample handlers and sampler handling systems that may be useful in the apparatus and method of the present invention are well known in the art. One example of an integrated handler and programmable station is the Beckman 1000 Laboratory Workstation TM robotic which may be adapted for use in the apparatus or method of the present invention.

In order to reduce carryover, the probe may have a conical tip. Use of silicone or other hydrophobic agent to coat the tip of the sampling probe may also be helpful to minimize sample carryover. Alternatively, the entire probe may be made of a hydrophobic material to reduce carryover. Suitable hydrophobic materials for used in the coating or for making the entire hydrophobic probe include: Teflon® (poly (tetrafluoroethylene) (PTFE)), Kynar® (polyvinylidene fluoride), Tefzel® (ethylene-tetrafluoroethylene copolymer), tetrafluoroethylene-perfluoroalkyl vinyl ether copolymer resin (PFA), a tetrafluoroethylene-hexafluoropropylene copolymer (EFP), polyether ether ketone (PEEK), etc.

In order to reduce sample carryover, a jet of gas, such as air, may be sprayed on the tip of the autosampler probe. The source of the jet of gas may be mounted either on the autosampler or near the autosampler. Another way to reduce sample carryover is to use a rinsing device that may be attached to the autosampler or be otherwise mounted on or near the flow cytometry apparatus of the present invention to rinse the autosampler probe between intakes of sample and/or buffer solution. The rinsing fluid may be water, a mild detergent, or a solvent, such as a solvent in which each of the particles in one or more of the samples is dissolved. When the particles are merely suspended in a suspension fluid, the rinsing fluid may be the same as the suspension fluid. The use of an autosampler with a sensing probe tip may improve the efficiency of sample uptake and performance by reducing carryover and ensuring reproducible sample volumes.

Various conventional peristaltic pumps may be used with the flow cytometry apparatus of the present invention. A preferred peristaltic pump is Gilson Minipuls 3. Preferably, a peristaltic pump of the present invention is operated in a manner that reduces pulsatile flow, thereby improving the sample characteristics in the flow cytometer. For example, a tubing length greater than 20 inches between pump and flow cytometer may be used or a linear peristaltic pump such as the Digicare LP5100 may be used to improve the sample characteristics.

Various types of tubing may be used for the fluid flow path of the present invention, as long as the tubing may function as high speed multi-sample tubing. When thin walled PVC (polyvinyl chloride) tubing is used as the tubing for the present invention, carryover between samples is substantially reduced compared to conventional peristaltic tubing. Preferably, the fluid flow path of the present invention is a single length of tubing without junctions. Such a single length of tubing reduces the breakup of bubbles and improves the performance in sample separation. A preferred type of high speed multi-sample tubing for use with the present invention is 0.01 to 0.03 inch inner diameter PVC tubing having a wall thickness of 0.01 to 0.03 inches. A particularly preferred tubing is 0.02 inch inner diameter PVC tubing having a wall thickness of 0.02 inch.

Various types of flow cytometers may be used with the flow cytometry apparatus of the present invention. Preferred types of flow cytometers are described in U.S. Pat. Nos. 5,895,764; 5,824,269; 5,395,588; 4,661,913; the entire contents and disclosures of which are hereby incorporated by reference. In the flow cytometer, samples may be sorted on a particle by particle basis using known methods. The flow cytometer may use software gating by light scatter to reduce the "noise" in the flow cytometer introduced by the periodic appearance of bubbles. The use of the real-time software in conjunction with flow cytometer controlling software may allow the samples from a given source well to be re-checked during sampling and data analysis to prove that "hits" from neighboring source wells do not arise from cross-contamination.

Flow cytometry, the measurement of cells in a moving liquid stream, is a valuable analysis tool in research laboratories. Conventional flow cytometry devices for sorting objects such as cells and particles basically consist of a liquid stream forming a sheath fluid into which cell sample is introduced then focused through an orifice. As the objects pass through the orifice, particular characteristics of the objects are determined based upon the analyzing or counting capabilities of the device. Usually, the device can sort or count at high speeds, collecting tens of thousands of the objects based on a variety of chemical and physical characteristics such as size, granulation of the cytoplasm and presentation of specific antigens. Accordingly, there has been considerable interest in flow cytometry to sort objects for subsequent analysis.

One commercially available flow cytometer which relies on a hydrodynamically focused fluid system is known as the FACScan™ instrument sold by Becton Dickinson Immunocytometry Systems, San Jose, Calif. The FACScan™ instrument rapidly analyzes cells on the basis of fluorescence and light scatter properties. Analysis is accomplished by introducing cells in a suspension to the center of a focused liquid stream thus causing them to pass, one at a time, through a focused light from a high powered laser. Each cell is individually characterized by its light scatter signals and by the intensity and color of fluorescence emitted while it is illuminated. This system is described in U.S. Pat. No. 4,844,610 issued Jul. 4, 1989 to North, U.S. Pat. No. 5,030,022 issued Jul. 9, 1991 to North and U.S. Pat. No. 5,040,890 issued Aug. 20, 1991 to North.

On-line data analysis may be used in the flow cytometer to compare data between well plates and facilitate overall utility of the data in conjunction with automation. Operation of the flow cytometer at higher pressure generally increases the sample flow rate and may, in some circumstances yield a higher throughput. Also, operation of the flow cytometer with increased time resolution in data software may allow resolution of samples at higher throughput rates.

Both peristaltic pumps and air bubbles have been used in a variety of detection devices with flowing samples. For example, bubbles are commonly used in clinical instruments to separate samples and the peristaltic pumps to move fluids. However, in flow cytometry there is specific teaching against air bubbles with the idea that, optimally, the bubbles should be removed from the sample prior to injection into the flow cytometer.

Using the flow cytometry apparatus of the present invention, it has already been possible to move and analyze at least 6 samples per minute. Preferably, the flow cytometry apparatus may be capable of moving and analyzing 60 samples per minute, even more preferably 120 samples per minute, and yet even more preferably 240 samples per minute.

Among the advantages of the flow cytometer apparatus of the present invention is that it allows rapid sampling of small volumes of sample. For example, a sample drawn into the fluid stream tubing at 10 rpm and flowing at a rate of ~3 ul/sec requires less than a 2 ul sample.

The throughput of the flow cytometry apparatus of the present invention tends to be more affected by the behavior of the autosampler rather than the characteristics of the peristaltic pump, the tubing or the flow cytometer. Thus, to the extent that an autosampler can move more rapidly from source well to source well, higher throughputs are achieved. Improved accuracy in volume intake/delivery by the autosampler leads to smaller sample volumes and improved throughputs.

EXAMPLE

Figure 2A:
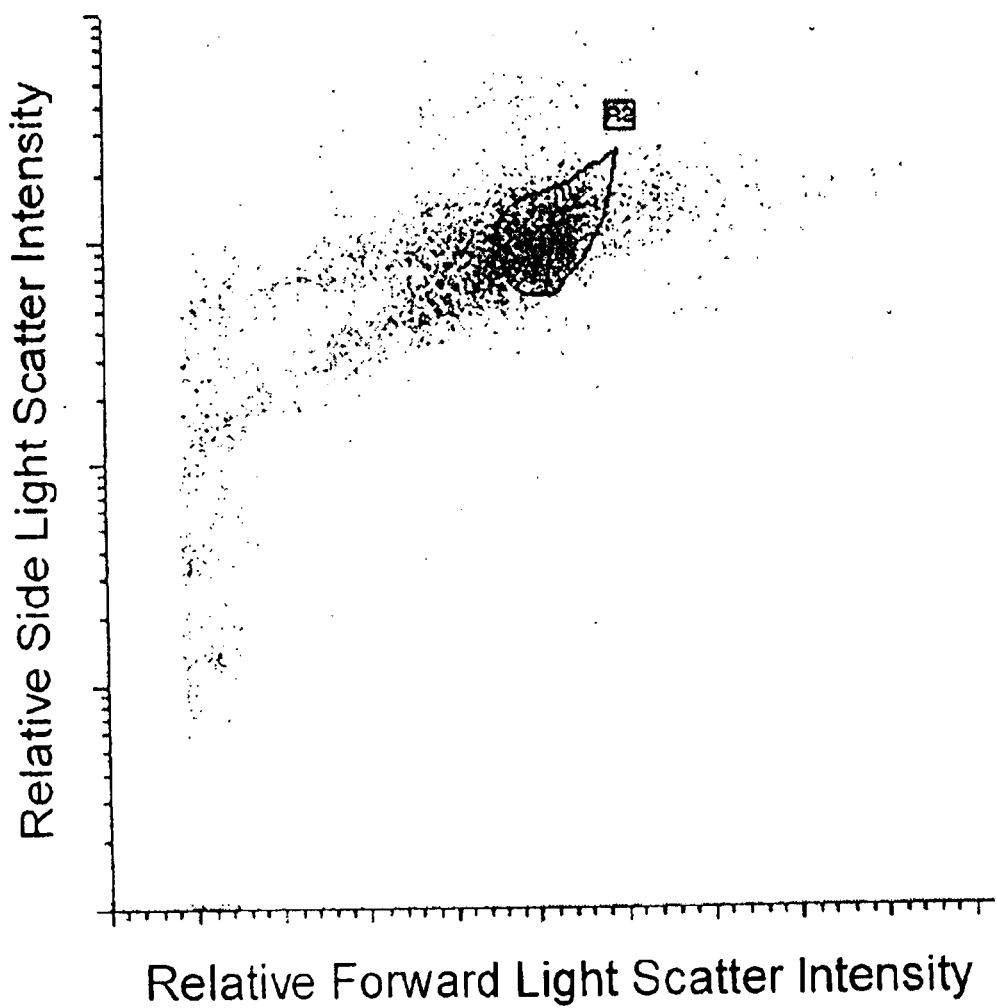
FIG. 2A illustrates the results of an experiment using a flow cytometry apparatus similar to that shown in FIG. 1A using 0.02 inches inner diameter PharMed TM tubing in terms of a graph of Forward Scatter vs. Side Scatter.
Figure 2B:
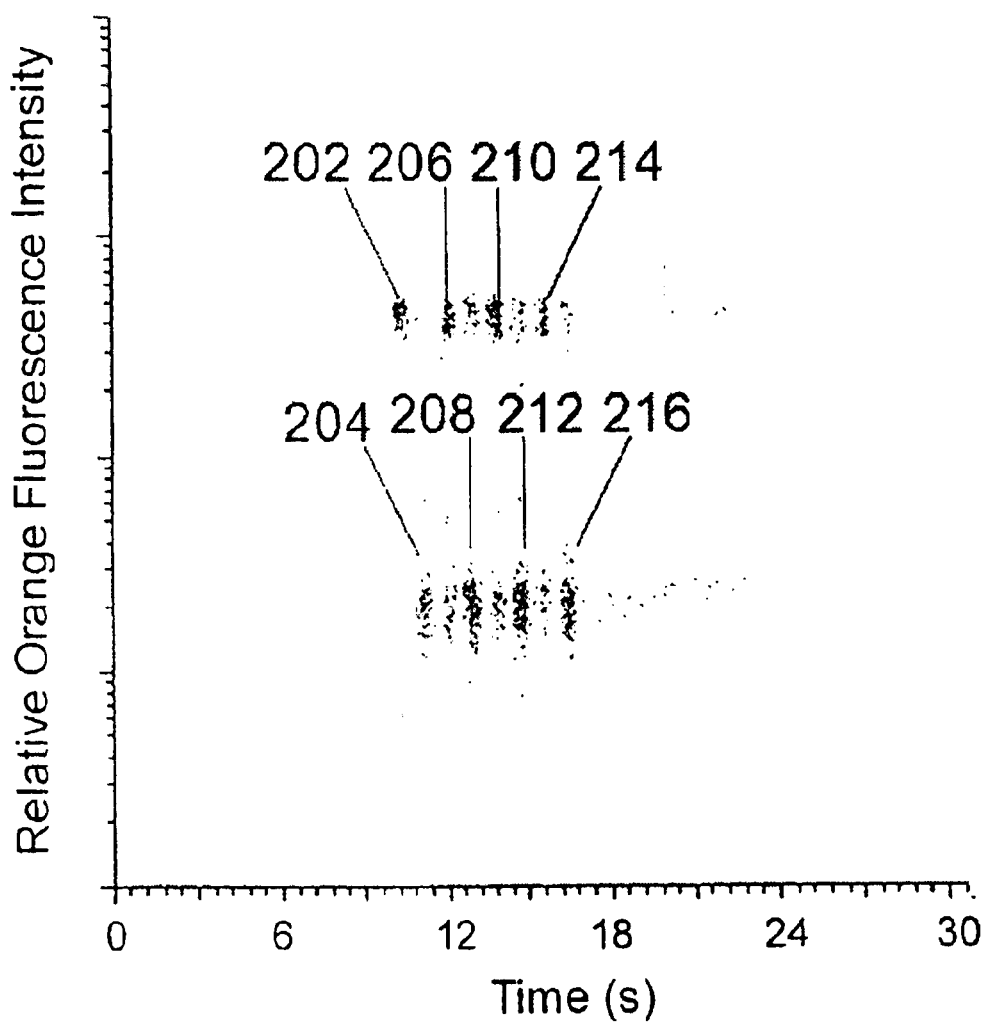
FIG. 2B illustrates the results of an experiment using a flow cytometry apparatus similar to that shown in FIG. 1A using 0.02 inches inner diameter PharMed TM tubing in terms of a graph of Fluorescence vs. Time (1024 channels= 60 seconds)
Figure 3A:
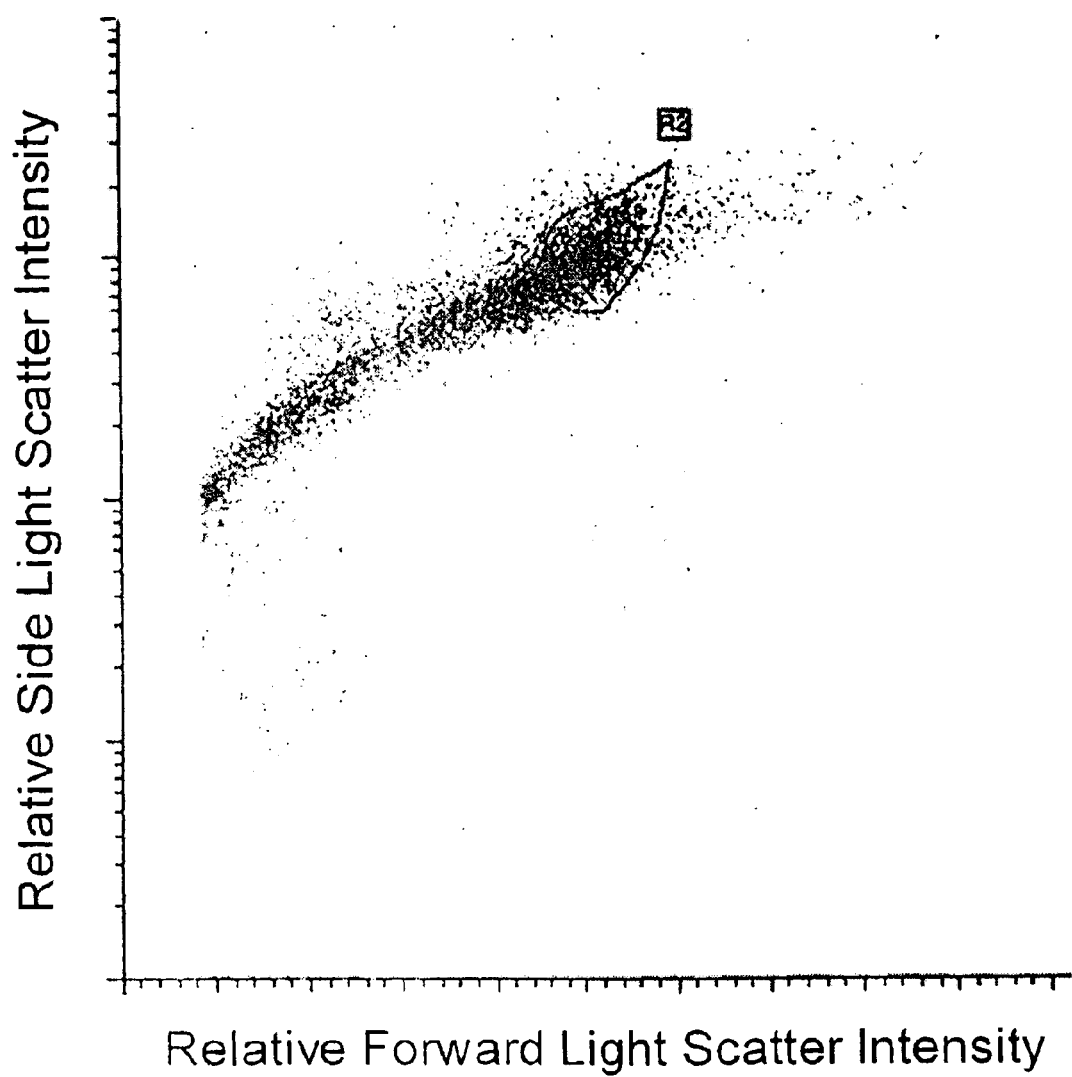
FIG. 3A illustrates the results of an experiment using a flow cytometry apparatus similar to that shown in FIG. 1A using Tygon TM PVC tubing S-54-HL in terms of a graph of Forward Scatter vs. Side Scatter.
Figure 3B:
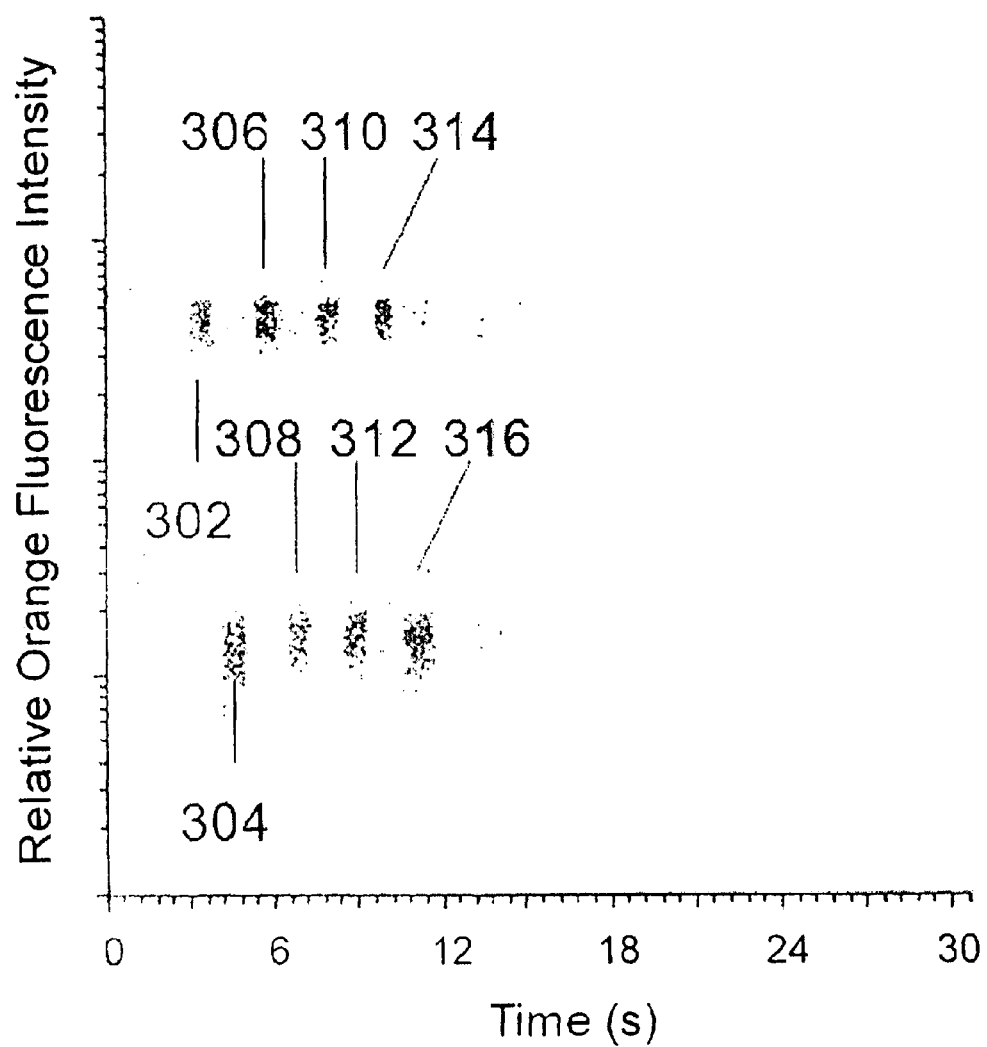
FIG. 3B illustrates the results of an experiment using a flow cytometry apparatus similar to that shown in FIG. 1A using Tygon TM PVC tubing S-54-HL in terms of a graph of Fluorescence vs. Time (1024 channels=60 seconds).

Using a flow cytometer apparatus set-up similar to that shown in FIG. 1A, commercial peristaltic tubing with thick walls (PharMed TM; 0.02 inch inner diameter, 3.69 mm outer diameter, polypropylene elastomer) was compared with another type (0.02 inch inner and 0.06 inch outer diameter Tygon Microbore TM, formulation S-54-HL) that had thin walls and was considerably stiffer. FIGS. 2A and 2B illustrate the flow cytometer results using the PharMed TM tubing to move samples 202, 206, 210, and 214 of Coulter Flow-Check beads having a proprietary fluorochrome as a fluorescence tag and four samples 204, 208, 212, and 216 of Flow Cytometry Standards Corporation having fluorescein as a fluorescence tag. FIG. 2A is a graph of Forward Scatter vs. Side Scatter with a gate around the particles aligned in the laser beam of the flow cytometer. FIG. 2B is a graph of Fluorescence vs. Time (1024 channels=60 seconds). The samples in FIG. 2 are moved through the tubing using a peristaltic pump operating at 10 RPM. FIGS. 3A and 3B illustrate the flow cytometer results using the PVC tubing to move samples 302, 306, 310, and 314 of Coulter Flow-Check beads having a proprietary fluorochrome as a fluorescence tag and four samples 304, 308, 312, and 316 of Flow Cytometry Standards Corporation beads having fluorescein as a fluorescence tag. FIG. 3A is a graph of Forward Scatter vs. Side Scatter with a gate around the particles aligned in the laser beam of the flow cytometer. FIG. 3B is a graph of Fluorescence vs. Time (1024 channels=60 seconds). The samples in FIG. 3 are moved through the tubing using a peristaltic pump operating at 10 RPM. As can be seen in FIG. 2B and FIG. 3B, the grouping of sample data points in FIG. 2B exhibit 27% carryover (particles between samples) compared to the groupings of sample data points in FIG. 3B that exhibit 5% carryover (particles between samples), indicating that the PVC tubing preserves the integrity of samples better than the PharMed TM tubing does.

Although the present invention has been fully described in conjunction with the preferred embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A flow cytometry apparatus for the detection of particles from a plurality of samples comprising:

means for moving the plurality of samples comprising particles from a plurality of respective source wells into a fluid flow stream, said means for moving the plurality of samples comprising a pump;

means for introducing a separation gas between each of said plurality of samples in said fluid flow stream; and a flow cytometer for hydrodynamically focusing said fluid flow stream and selectively analyzing said particles in each of said plurality of samples as said fluid flow stream passes through said flow cytometer.

2. The flow cytometry apparatus of claim 1, wherein said means for moving said plurality of samples further comprises an autosampler.

3. The flow cytometry apparatus of claim 2, wherein said autosampler includes a probe and said flow cytometry apparatus includes a means for exposing a probe tip of said probe to a jet of gas to remove liquid from said probe tip.

4. The flow cytometry apparatus of claim 2, wherein said autosampler includes a probe having a conical tip.

5. The flow cytometry apparatus of claim 2, wherein said autosampler includes a hydrophobic probe.

6. The flow cytometry apparatus of claim 5, wherein said probe comprises a hydrophobic material.

7. The flow cytometry apparatus of claim 5, wherein said probe is coated with a hydrophobic material.

8. The flow cytometry apparatus of claim 1, wherein said pump comprises a peristaltic pump.

9. The flow cytometry apparatus of claim 8, wherein a portion of said fluid flow stream passing through said peristaltic pump is contained within a high speed multi-sample tube.

10. The flow cytometry apparatus of claim 8, further comprising a single length of tubing extending from said autosampler to said flow cytometer.

11. The flow cytometry apparatus of claim 10, wherein said single length of tubing comprises a high speed multi-sample tube.

12. The flow cytometry apparatus of claim 11, wherein said high speed multi-sample tube comprises a poly vinyl chloride tube.

13. The flow cytometry apparatus of claim 11, wherein said high speed multi-sample tube comprises a poly vinyl chloride tube having an inner diameter of about 0.02 inches and a wall thickness of about 0.02 inches.

14. The flow cytometry apparatus of claim 8, wherein a portion of said fluid flow stream passing through said peristaltic pump is contained within a tube having an internal diameter of 0.02 inches.

15. The flow cytometry apparatus of claim 1, wherein said separation gas comprises air.

16. The flow cytometry apparatus of claim 1, wherein said plurality of samples are homogenous.

17. The flow cytometry apparatus of claim 1, wherein said plurality of samples are heterogeneous.

18. The flow cytometry apparatus of claim 1, wherein said particles comprise biomaterials.

19. The flow cytometry apparatus of claim 18, wherein said biomaterials are fluorescently tagged.

20. The flow cytometry apparatus of claim 1, further comprising a well plate including said plurality of respective source wells.

21. The flow cytometry apparatus of claim 20, wherein said well plate includes at least 96 source wells.

22. The flow cytometry apparatus of claim 20, wherein said well plate includes at least 384 source wells.

23. The flow cytometry apparatus of claim 20, wherein said well plate includes at least 1536 source wells.

24. The flow cytometry apparatus of claim 20, wherein said well plate includes wells having a conical shape.

25. The flow cytometry apparatus of claim 20, wherein said well plate is mounted in an inverted position.

26. The flow cytometry apparatus of claim 1, further comprising a means for injecting a buffer fluid between adjacent samples in said fluid flow stream so that said adjacent samples are separated by two bubbles of separation gas and said buffer fluid located between said two bubbles of separation gas.

27. The flow cytometry apparatus of claim 1, wherein at least one said plurality of samples includes a drug present therein.

28. The flow cytometry apparatus of claim 1, wherein a portion of said fluid flow stream passing through said pump is contained within a tube having an internal diameter of 0.02 inches.

29. A flow cytometry apparatus for the detection of particles from a plurality of samples, comprising:
 a pump for moving the plurality of samples comprising particles from a plurality of respective source wells into a fluid flow stream;
 separation means for introducing a parameter-controlled separation gas between each of said plurality of samples in said fluid flow stream; and
 a flow cytometer for hydrodynamically focusing said fluid flow stream and selectively analyzing said particles in each of said plurality of samples as said fluid flow stream passes through said flow cytometer, said separation gas having parameters of predetermined values to permit the hydrodynamic focusing of said fluid flow stream in said flow cytometer,
 said separation means including tubing of a given size for introducing separation gas aliquots of a controlled volume into said fluid flow stream with said samples flowing at a specific rate, said given size and said controlled volume and said specific rate all being predetermined to permit the hydrodynamic focusing of said fluid flow stream in said flow cytometer.

30. The flow cytometry apparatus of claim 29, wherein said separation means includes tubing extending from said pump and having compression characteristics allowing said pump to move samples separated by gas through said tubing at a speed of at least 6 samples per minute without causing adjacent samples to mix with one another.

31. The flow cytometry apparatus of claim 30, wherein said tubing has an inner diameter of less than about 0.03 inch.

32. The flow cytometry apparatus of claim 31, wherein said inner diameter is greater than about 0.01 inch.

33. The flow cytometry apparatus of claim 29, wherein said given size is less than about 0.03 inch.

34. The flow cytometry apparatus of claim 29, wherein said specific rate is at least six samples per minute.

* * * * *

UNITED STATES PATENT AND TRADEMARK OFFICE
CERTIFICATE OF CORRECTION

PATENT NO. : 6,890,487 B1
APPLICATION NO. : 09/501643
DATED : May 10, 2005
INVENTOR(S) : Larry A. Sklar et al.

It is certified that error appears in the above-identified patent and that said Letters Patent is hereby corrected as shown below:

Column 1, Lines 15-17: Change "This invention is made with government support under contract number NIH 1R24 GM 60799 (Project Number 3).The government may have certain rights in this invention." to --This invention was made with Government support under Grant No. GM060799 (EB000264), awarded by the National Institutes of Health. The government has certain rights in this invention.--

Signed and Sealed this

Second Day of December, 2008

JON W. DUDAS
*Director of the United States Patent and Trademark Office*